United States Patent [19]
Jettka et al.

[11] Patent Number: 6,103,274
[45] Date of Patent: *Aug. 15, 2000

[54] PHARMACEUTICAL, ORALLY APPLICABLE COMPOSITION

[75] Inventors: Winfred Jettka; Jörg-Christian Hager, both of Köln; Manfred Dürr, Bergheim-Glessen, all of Germany

[73] Assignee: Rhone-Poulenc Rorer GmbH, Cologne, Germany

[*] Notice: This patent is subject to a terminal disclaimer.

[21] Appl. No.: 09/162,574

[22] Filed: Sep. 29, 1998

Related U.S. Application Data

[63] Continuation of application No. 08/685,377, Jul. 23, 1996, Pat. No. 5,858,413.

[30] Foreign Application Priority Data

Aug. 14, 1995 [DE] Germany .......................... 195 29 862

[51] Int. Cl.⁷ .......................... A61K 33/06; A61K 33/08; A61K 33/10; A61K 33/12
[52] U.S. Cl. .......................... 424/682; 424/604; 424/653; 424/683; 424/686; 424/687; 424/688; 424/689; 424/690; 424/692; 424/715; 514/23; 514/574; 514/819
[58] Field of Search .................... 424/682, 604, 424/653, 683, 686, 687, 688, 689, 690, 692, 715; 514/23, 574, 819

[56] References Cited

U.S. PATENT DOCUMENTS

| | | | |
|---|---|---|---|
| 3,041,239 | 6/1962 | Nashed | 167/65 |
| 5,173,305 | 12/1992 | Grimberg | 424/682 |
| 5,409,907 | 4/1995 | Blase et al. | 514/54 |

FOREIGN PATENT DOCUMENTS

| | | |
|---|---|---|
| 0 138 540 | 4/1985 | European Pat. Off. . |
| 0 264 187 | 4/1988 | European Pat. Off. . |
| 1176195 | 1/1970 | United Kingdom . |

*Primary Examiner*—Phyllis G. Spivack
*Attorney, Agent, or Firm*—Proskauer Rose LLP

[57] ABSTRACT

A pharmaceutical, orally applicable composition is disclosed, whereby the composition contains at least one antacid active substance as well as more than 45% by weight of a sugar and/or sugar alcohol and between 12% and 35% by weight of water. The composition has a liquid or a semisolid consistency and is substantially free of preservatives.

14 Claims, No Drawings

PHARMACEUTICAL, ORALLY APPLICABLE COMPOSITION

This application is a continuation of U.S. patent application Ser. No. 08/685,377, filed Jul. 23, 1996, now issued as U.S. Pat. No. 5,858,413.

FIELD OF THE INVENTION

The present invention is directed to a pharmaceutical, orally applicable composition containing at least one antacid active substance, a sugar or sugar alcohol, and a pharmaceutically harmless solvent, with the composition having a liquid to semisolid consistency.

BACKGROUND OF THE INVENTION

Orally applicable, pharmaceutical compositions with at least one antacid active substance are known and available in the trade for a long time. Depending on each active substance, or on each active substance mixture, these known antacids are employed as tablets, as coated tablet or as powder for the prophylaxis and/or for the treatment of stomach troubles, particularly for the treatment of sickness, stomach cramps, heartburn, sensation of eating to excess, belching, vomiting, bloating, gastric ulcer and/or for the treatment of trouble after the abuse of alcohol or nicotine. Heretofore it has been necessary for the patient to thoroughly chew the corresponding tablet or the coated tablet before swallowing, which often leads to an adhesion of components of the tablet, or the coated tablet, in the dental area and/or palate area of the mouth, which a lot of patients do not like and accordingly do not employ such compositions, even though it is necessary.

In order to solve these problems for the application of the known pharmaceutical compositions, it was already tried to provide a liquid suspension of the active substance, whereby such suspensions are offered in their liquid form to the patient. However, the known liquid compositions contain a relatively high proportion of aromatic substances in order to avoid the bad taste of the antacid active substances. Moreover the known liquid suspensions require a preservative, whereby the preservatives used heretofore either diminish drastically the taste of the known liquid composition, and/or are suspected of being carcinogenic.

SUMMARY OF THE INVENTION

The present invention has as its object to provide a liquid or semisolid pharmaceutical composition with an antacid active substance, whereby the composition has a particularly pleasant taste.

This object is realized according to the invention by a pharmaceutical composition containing at least one antacid substance, a sugar or sugar alcohol, and a pharmaceutically harmless solvent, the composition having a liquid to semisolid consistency and being substantially free of any preservatives.

The inventive composition contains, as the initially mentioned prior art, at least one antacid active substance, or antacid active substance mixture, and moreover further ingredients. An essential aspect of the inventive composition is that the inventive composition has a liquid to semisolid consistency, but the inventive composition is substantially free of preservatives. Moreover the inventive composition contains as further ingredients more than 45% by weight of a sugar and/or a sugar alcohol, relative to the ready-to-use composition, and up to 40% by weight of a pharmaceutically harmless solvent, relative to the ready-to-use composition.

The inventive composition has a number of advantages. A first advantage is that the inventive composition is particularly easy to use due to its liquid to semisolid consistency, since the aforedescribed problems of the known solid composition do not occur because it is not necessary to crush the inventive composition in the mouth. The inventive composition allows, because of its liquid to semisolid consistency, an individual dosage, which is also not so easily realizable in the known compositions. Because the inventive composition is generally free of any preservatives, problems of taste do not occur in the liquid to semi-solid composition of the present invention, as occur in the case of the known suspensions do not occur in such a liquid or semisolid, inventive composition, as is the case for the known suspensions. In the inventive composition the bad taste coming from the antacid active substance, respectively the antacid active substance mixture, is concealed by the fact that the inventive composition contains at least 45% by weight of a sugar and/or a sugar alcohol. The sugar, or sugar alcohol in the inventive composition not only conceals the bad taste of the active substance, but also gives a pleasant taste to the inventive composition even when the inventive composition contains small amounts of a preservative, as for example 0.01% by weight to about 0.1% by weight. It was surprisingly noted that the inventive composition is microbiologically stable and thus autosterile even without any preservative, whereby this advantageous property of the inventive composition occurs due to the high concentration of the sugar or sugar alcohol. Despite the relatively large portion of sugar, or sugar alcohol, the inventive composition does not exhibit sedimentation or clumping of the antacid active substance or the active substance mixture, so that the liquid to semisolid inventive composition is stable in itself. Thus it is not necessary to shake the inventive composition before being taken in order to promote homogeneity of the active substance or the active substance mixture. Furthermore the liquid to semisolid consistency of the inventive composition allows the antacid active substance, or the active substance mixture to spread, after it is taken, very rapidly and homogeneously over the patient's stomach and the intestinal tract, so that the inventive composition leads to rapid pain diminution and to rapid curing. Due to its liquid to semisolid formulation the inventive composition can also be dispensed very precisely and reproducibly, or it can be packed in single doses, so that correspondingly the manufacturing process is standardised.

DETAILED DESCRIPTION OF THE INVENTION

A first embodiment of the inventive composition is characterized in that the solid substance content of the liquid to semisolid composition is at most 88% by weight, relative to the final composition. Such an embodiment of the inventive composition contains as active substances at least one antacid active substance, or the active substance mixture, as well as the sugar and/or the sugar alcohol in the aforementioned concentration, whereby the inventive composition contains as suspending agent, or as emulsifier, at least 12% by weight of the above mentioned pharmaceutically harmless solvent, relative to the final composition. In such an embodiment having a high solid substance content, it was surprisingly noted that a clumping and/or sedimentation of the antacid active substance does not occur, even when the solid substance content varies between 65% by weight and 88% by weight, relative to the final composition. Such an embodiment provides for a homogeneous composition and a regular distribution of the antacid active substance, or active substance mixture, even after a storage time of several months.

In respect to the solvent that the inventive composition contains, it is to be noted that this is specifically a pharmaceutically harmless solvent. The inventive composition preferably contains as solvent water, ethanol, propanol-1 and/or propanol-2 alone or as mixtures thereof, whereby of the afore-mentioned solvents water is preferred because of its absolute harmlessness. Within the present invention the term water means all watery systems.

A particularly suitable and highly effective inventive composition contains as pharmaceutically harmless solvent between 12% by weight and 35% by weight of water, relative to the ready-to-use composition. This embodiment of the inventive composition is particularly pleasant to consume, since this embodiment has a very neutral taste, and especially because the unpleasant characteristic taste of the antacid active substance, or active substance mixture, is concealed completely by the high concentration of sugar and/or sugar alcohol. In such a watery, liquid to semisolid formulation of the inventive composition a flocculation of the active substance, or the active substance mixture, or a phase separation of the composition is not noted, even if the inventive composition is stored for a long time without being shaken.

Also in respect to the concentration of the antacid active substance, or the antacid active substance mixture, in the inventive composition, it is to be noted that this concentration depends on which daily doses are used in the inventive composition. The inventive composition contains particularly between 5% by weight and 43% by weight, preferably between 12% by weight and 30% by weight, of the antacid active substance, whereby these aforementioned concentrations each relate to the final composition.

In respect to the at least one antacid active substance, or the antacid active substance mixture, that the inventive composition contains, it is to be noted that this is a known antacid active substance, preferably aluminum hydroxide, magnesium hydroxide, magnesium trisilicate, magnesium carbonate, magnesium phosphate, calcium carbonate, calcium phosphate, sodium citrate, magnesium oxide, magaldrate, $(Al_5Mg_{10}(OH)_{31}(SO_4)_2 \times H_2O)$ hydrotalcite, sodium hydrogencarbonate and/or bismuth subcarbonate, whereby the aforementioned active substance concentrations refer to the anhydrous active substance.

As it is already mentioned above, the inventive composition contains as further ingredient more than 45% by weight of the sugar and/or the sugar alcohol, relative to the final composition. In the inventive composition the concentration of the sugar and/or the sugar alcohol varies between 45% by weight and 80% by weight, preferably between 60% by weight and 80% by weight. Despite this relatively high concentration of sugar and/or sugar alcohol in the inventive composition, the liquid to semisolid form of the inventive composition additionally has excellent stability, so that a flocculation, clumping or precipitation of the antacid active substance, or the antacid active substance mixture, does not occur during the manufacturing process nor during extremely long storage periods.

Moreover the aforementioned embodiments of the inventive composition that have a sugar content, or a sugar alcohol concentration, of between 45% by weight and 80% by weight, have an extremely pleasant taste and they are furthermore autosterile, so that the patients, particularly juvenile patients, like to use them.

Within the present application the term sugar means all known monosaccharides, disaccharides and/or oligosaccharides, preferably, sucrose (saccharose), glucose, fructose, maltose, lactose, galactose and/or starch hydrolyzates that are usual in the pharmaceutical industry. An embodiment of the inventive composition is characterized in that it particularly contains sucrose as sugar.

Within the present application the term alcohol sugar means all known monomer, dimer and oligomer hydrogenated sugars, preferably, sorbitol, manitol, xylitol, malitol (glucosyl-2(1+4)-D-glucitol) and/or hydrogenated starch hydrolyzates that are usual in the pharmaceutical industry.

A particularly suitable embodiment of the inventive composition contains sorbitol, xylitol and/or malitol in the aforementioned concentrations as sugar alcohol. This embodiment is particularly characterized in that it has an extremely pleasant taste and a high microbiological stability, so that this embodiment of the inventive composition is taken willingly and without problems.

In order to make consumption of the inventive composition easier, a particularly advantageous development of the inventive composition is characterized in that it has a gelatinous consistency. Particularly if such a gelatinous composition is packed in single doses, for example packed and sealed in corresponding bags, the patient can, if necessary, use a measured amount of the inventive composition very rapidly and simply, without risking a loss of a part of the inventive composition.

In respect to the further ingredients of the inventive composition, it is to be noted that these are such pharmaceutically usual ingredients that are present in a liquid to semisolid composition. In order to guarantee, for example, a desired consistency in the inventive composition, as for example the aforementioned gelatinous consistency, the inventive composition can contain at least one suitable thickening agent, particularly between 0.2% by weight and 2% by weight, such as xanthan gum, guar gum and/or cellulose derivatives, preferably microcrystralline cellulose, methyl cellulose, hydroxyethyl cellulose, methylhydroxypropyl cellulose and/or hydroxypropyl cellulose. Furthermore it is advisable that the inventive composition also contains between 2% by weight and 8% by weight glycerol as well as between 0.05% by weight and 0.7% by weight of an aromatic substance.

A particularly suitable formulation of the inventive composition contains as main substances 12% by weight–28% by weight of the antacid active substance, or the active substance mixture, 46% by weight–58% by weight of the sugar and/or sugar alcohol, as well as 18% by weight–30% by weight of water, whereby this composition may also contain 0–10% by weight of further components, particularly glycerol, thickening agents and/or aromatic substances.

The inventive composition is described in more detail by the following three examples.

EXAMPLE 1

A gelatinous formulation was manufactured that contained the following ingredients:

13.33 g aluminum oxide, hydrous, with a concentration of about 50% by weight of $Al_2O_3$ (dry);

13.33 g magnesium hydroxide powder, anhydrous;

52.5 g sorbitol solution, 70% by weight in water, not crystallizing;

15.0 g malitol solution, 80% by weight in water (Lycasine™, an artificial sweetener available from Roquette Corporation of New York);

5.34 g glycerol, 85% by weight;

0.35 g xanthan gum; and
0.15 g aromatic substances.

For the manufacturing of this gelatinous formulation, the glycerol was first added to the solution of the sugar alcohols. Thereafter, the hydrous aluminum oxide as well as the magnesium hydroxide were suspended into this mixture. The aromatic substances were added to the mixture after thoroughly stirring it and then the mixture was thickened with the xanthan gum.

The gelatinous formulation manufactured that way had a concentration of antacid active substances of 26.7% by weight, a water content of 19.6% by weight as well as a sugar alcohol content of 48.8% by weight, whereby all these concentrations relate to the final composition.

EXAMPLE 2

A second gelatinous formulation was manufactured that has the following main components:
10.00 g aluminum oxide, hydrous, with a solid substance content of $Al_2O_3$ of 50% by weight;
10.00 g magnesium hydroxide powder, anhydrous;
79.86 g sugar syrup (64% by weight of dry substance); and
0.14 g aromatic substances.

For the manufacturing of this formulation the aqueous sugar syrup was prepared. The hydrous aluminum oxide and the magnesium hydroxide powder were suspended into this aqueous sugar syrup. Subsequently the aromatic substances were added. After thoroughly stirring, a gelatinous formulation appeared that had a concentration of antacid active substance mixture of 20% by weight (calculated as anhydrous substance), a water content of 28.7% by weight and a sugar content of 51.1% by weight (calculated as anhydrous substance), each relative to the final composition.

EXAMPLE 3

A third semisolid formulation was manufactured, whereby this semisolid formulation contained the following ingredients:
13.3 g calcium carbonate;
62.0 g sorbitol solution in water, 70% by weight, not crystallizing;
17.8 g malitol solution in water, 80% by weight (Lycasine™);
6.31 g glycerol, 85% by weight;
0.42 g xanthan gum; and
0.17 g aromatic substances.

The manufacturing according to example 3 was carried out exactly as described above for the manufacturing of the composition according to example 1.

The ready-to-use, semisolid formulation 3 contained a concentration of 13.3% by weight of the antacid active substance (calculated as anhydrous substance), 22.3% by weight of water as well as 57.6% by weight of the sugar alcohol (calculated as anhydrous substance).

For verifying its acceptability, the gelatinous formulation according to example 1 that had the highest concentration of bitter tasting antacid active substances, was distributed to 50 as was a prior art suspension.

In order to objectify this taste examination, the 50 test-persons received firstly three times the formulation according to example 1, whereby one week was determined as the time period between the single tests.

After a taste-neutralizing phase, which means a break of three hours and the repeated drinking of water, the prior art suspension was then given to the test-persons.

In each of the three tests, 47 test-persons reported that the formulation according to example 1 had an essentially better taste than the usual suspension, while 44 test-persons also reported that the formulation according to example 1 did not produce a sweet aftertaste a few minutes after tasting.

The aforedescribed 3-phase-test was repeated after one month, whereby the same test-persons firstly tasted the prior art suspension and after a break of three hours they tasted the formulation according to example 1 while repeatedly drinking water.

In this case, 49 persons reported unanimously that the formulation according to example 1 had an essentially better taste, whereas the prior art suspension had an unpleasant taste despite rinsing several times with water.

In order to prove the microbiological stability of the formulation according to example 1 the following examination was carried out:

The formulation according to example 1 was subjected to the antimicrobial preservation test according to DAB 10, 3. postscript 1994 (the 10th editions of *Deutsches Arzneibuch*, a German compendium of pharmaceutical products).

The results of this test art indicated in the following table, whereby the inoculation was carried out with 0.3 ml of germ suspension.

TABLE 1

| stock culture | seed strain | number of bacteria per g/ml after a period of | | | |
|---|---|---|---|---|---|
| | | immediately | 14 days | Red.F. | 28 days |
| 1 | 4.909.000 | 4.800.000 | 240 | $10^4$ | 230 |
| 2 | 4.991.000 | 800.000 | 230 | $10^4$ | 260 |
| 3 | 3.569.000 | 275.680 | 200 | $10^4$ | 250 |
| 4 | 3.169.000 | 36.036 | 220 | $10^4$ | 250 |
| 5 | 1.500.000 | 900.000 | 180 | $>10^3$ | 100 |
| 6 | 3.918.000 | 1.703.000 | 200 | | 164 |
| 7 | 1.455.000 | 53.423 | 250 | | 800 |
| 8 | | 250 | 200 | | 170 |

1 = *Staph. aureus*
2 = *Escherichia coli*
3 = *Ps. aeruginosa*
4 = *Candida albicans*
5 = *Aspergillus niger*
6 = *Zygosacch. rouxii*
7 = dirty water
8 = control, not inoculated

What is claimed is:

1. A pharmaceutical antacid composition for oral use, comprising:
    (a) between 5% and 30% by weight of at least one antacid active substance, selected from the group consisting of aluminum hydroxide, magnesium hydroxide, magnesium trisilicate, magnesium carbonate, magnesium phosphate, calcium carbonate, calcium phosphate, sodium citrate, magnesium oxide, magaldrate, hydrotalcite, sodium hydrogencarbonate, bismuth subcarbonate and mixtures thereof;
    (b) more than 45% by weight of a sugar or a sugar alcohol; and
    (c) between 12% and 35% by weight of water,
    wherein said composition has a liquid or a semisolid consistency and is substantially free of preservatives.

2. The pharmaceutical composition of claim 1, wherein said composition has a solids content of up to 88% by weight.

3. The pharmaceutical composition of claim 1, comprising between more than 45% and 80% by weight of said sugar or sugar alcohol.

4. The pharmaceutical composition of claim 1, comprising between about 48% by weight and about 70% by weight of said sugar or sugar alcohol.

5. The pharmaceutical composition of claim 1, wherein said sugar alcohol is selected from the group consisting of sorbitol, manitol, xylitol, maltitol, hydrogenated starch hydrolyzates, and mixtures thereof.

6. The pharmaceutical composition of claim 1, wherein said sugar is selected from the group consisting of sucrose, glucose,.fructose, maltose, lactose, galactose, starch hydrolyzates, and mixtures thereof.

7. The pharmaceutical composition of claim 1, which has a gelatinous consistency.

8. The pharmaceutical composition of claim 1 further comprising pharmaceutically harmless excipients.

9. The pharmaceutical composition of claim 8, wherein said excipients are selected from the group consisting of glycerol, at least one thickening agent, at least one aromatic substance, and mixtures thereof.

10. The pharmaceutical composition of claim 9, wherein said composition comprises up to 8% by weight of glycerol and up to 2% by weight of said thickening agent.

11. The pharmaceutical composition of claim 9, wherein said excipients comprise between about 2% and 8% by weight of glycerol, between about 0.2% by weight and about 2% by weight of a thickening agent, and between about 0.05% by weight and about 0.7% by weight of an aromatic substance.

12. The pharmaceutical composition of claim 9, wherein said thickening agent is selected from the group consisting of xanthan gum, guar gum, cellulose, and mixtures thereof.

13. The pharmaceutical composition of claim 9, wherein said thickening agent comprises microcrystalline cellulose, methyl cellulose, hydroxyethyl cellulose, methylhydroxypropyl cellulose, hydroxypropyl cellulose, and mixtures thereof.

14. The pharmaceutical composition of claim 1 comprising between 46% and 58% by weight of said sugar or sugar alcohol.

* * * * *